United States Patent [19]

Bahrmann et al.

[11] Patent Number: 5,126,475
[45] Date of Patent: Jun. 30, 1992

[54] PROCESS FOR THE PREPARATION OF ORGANIC PHOSPHITES WHICH ARE STABLE TO HYDROLYSIS

[75] Inventors: Helmut Bahrmann, Hamminkeln; Bernhard Fell; Georgios Papadogianakis, both of Aachen, all of Fed. Rep. of Germany

[73] Assignee: Hoechst Aktiengesellschaft, Fed. Rep. of Germany

[21] Appl. No.: 632,465

[22] Filed: Dec. 21, 1990

[30] Foreign Application Priority Data

Dec. 23, 1989 [DE] Fed. Rep. of Germany ....... 3942787

[51] Int. Cl.⁵ .............................................. C07F 9/141
[52] U.S. Cl. ...................................... 558/85; 558/95; 558/177
[58] Field of Search .......................... 558/85, 177, 95

[56] References Cited

U.S. PATENT DOCUMENTS 4,312,818  1/1982  Maul et al. ......................... 558/95

FOREIGN PATENT DOCUMENTS 2465740  3/1981  France ................................. 568/85

Primary Examiner—James H. Reamer
Attorney, Agent, or Firm—Jordan B. Bierman

[57] ABSTRACT

Preparation of phosphites which are stable to hydrolysis from organic phosphites or phosphorus-halogen compounds and an ammonium salt of a hydroxysulfonic acid which is insoluble in water and soluble in an organic solvent. The compounds are useful in making catalysts for the hydroformylation reaction.

15 Claims, No Drawings

PROCESS FOR THE PREPARATION OF ORGANIC PHOSPHITES WHICH ARE STABLE TO HYDROLYSIS

This Application claims the priority of German Application P 39 42 787.0, filed Dec. 23, 1989.

The invention relates to a process for the preparation of organic phosphites which are stable to hydrolysis and form soluble ammonium salts in organic media.

BACKGROUND OF THE INVENTION

Phosphorous acid triesters (organic phosphites) are compounds which are sensitive to oxidation and can easily be hydrolyzed. They are used as antioxidants in lubricants, where they collect oxygen and are oxidized to phosphates. As stabilizers for polyvinyl chloride, their action is based on the fact that, under the influence of air, UV rays, and/or heat, they are capable of bonding the hydrogen chloride liberated from the polymer (compare, for example, British Patent 803,557 and U.S. Pat. No. 3,516,963).

As well as being used as antioxidants in lubricants and stabilizers in organic polymers, organic phosphites are used as co-catalysts in hydroformylation. Rhodium/phosphite catalyst systems are highly active in this reaction, and are especially suitable for olefins which are difficult to hydroformylate, such as n-butene-2, 2-methylpropene, vinyl acetate, cyclohexene, acrolein and acrylonitrile.

Organic phosphites are very sensitive to hydrolysis; they are hydrolyzed with water (more rapidly in the presence of bases, and still more rapidly by aqueous acids) to give phosphorous acid diesters (secondary phosphites), as well as monoesters (primary phosphites) or free phosphorous acid. In the course of time, even traces of water can thus deactivate the Rh/phosphite system employed as the hydroformylation catalyst.

The rate of hydrolysis depends greatly on the nature of the ester radicals. Trimethyl phosphite is the most unstable; as the chain length increases, the phosphites become more stable to hydrolytic influences. According to A. E. Arbusov and M. G. Imaev [C.A. 51, 1374 g (1957], the rate of hydrolysis of triphenyl phosphite lies between that of triethyl phosphite and that of tripropyl phosphite.

M. G. Imaev [C.A. 55 24531 f (1961)] found that the addition of organic and inorganic bases retards the hydrolysis of trialkyl phosphites, and triethylamine has a better action than pyridine. The author assumes that, by formation of a salt, the base collects the secondary phosphite initially formed and in this way delays further hydrolysis.

European Patent 285,136 A2 describes a process for the separation of secondary and tertiary phosphites. For this, water and an amine are added to a solution of the phosphites in an organic solvent. The salt of the primary phosphite is formed from the secondary phosphite and the tertiary phosphite is separated therefrom.

European Patent 149,894 A2 relates to a hydroformylation process in which a rhodium complex compound containing carbon monoxide and, as a further ligand, a cyclic phosphite is employed as the catalyst. A tertiary amine is also added to the catalyst to stabilize the phosphite. This collects acid cleavage products, which are formed by acid hydrolysis of these cyclic phosphites during the hydroformylation and deactivate the catalyst. The cleavage products also catalyze further hydrolysis of the phosphites. According to European Patent 149,894 A2, the ability of tertiary amines to stabilize the cyclic phosphites extends to cyclic phosphites but not to acyclic (open-chain) phosphites.

Y. Matsui [Bulletin of the Japan Petroleum Institute 19, No. 1, pages 62–67 (1977)] employed the system RhH(CO) (PPh$_3$)$_3$/P(OPh$_3$) as a hydroformylation catalyst. The life of this catalyst was only four hours. After addition of tri-n-octylamine, it was possible to increase this life to more than 10 hours. The action of the amines is based on collection of the acid cleavage products of the phosphites. They are reported to stabilize the catalyst by preventing the cleavage products of the phosphites from forming coordination complexes with the rhodium.

European Patents 167,969 A2 and 143,464 B1 describe phosphites with additions of amines which have a greater stability to water than the same phosphites without added amine.

Japanese Patent Application 81/113,790 describes the influence of diethanoldodecylamine on the hydrolysis of distearylpentaerythritol diphosphite. A mixture of 100 parts by weight of phosphite and 5 parts by weight of amine absorbs 7.1% water within 96 hours at 20° C. and 90% relative humidity. Under otherwise identical conditions—but without addition of amine—the phosphite absorbs 21.4% water.

BRIEF DESCRIPTION OF THE INVENTION

Therefore, it is the object of the invention to provide a process which facilitates preparation of organic phosphites which are stable to hydrolysis. It comprises reacting organic phosphites (phosphorous acid triesters) or phosphorous-halogen compounds of the formulas PX$_3$ or (R$^3$O)PX$_2$(in which X is chlorine, bromine, or iodine, and R$^3$ is optionally substituted aliphatic, cycloaliphatic, or aromatic hydrocarbon radical) with at least the equivalent amount of an ammonium salt of a hydroxysulfonic acid which is insoluble in water and soluble in an organic solvent.

Hydroxysulfonic acids of the invention are organic compounds which contain both at least one hydroxyl (—OH) and at least one sulfonic acid group (—SO$_3$H). These compounds are represented by Formula I.

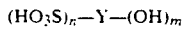

$$(HO_3S)_n-Y-(OH)_m \qquad I$$

in which Y is an organic radical, m is an integer from 1 to 3, and n is an integer from 1 to 4. They accordingly include sulfonated hydroxy compounds which are derivatives of aliphatic, cycloaliphatic, aromatic, and heterocyclic radicals. The aliphatic compounds can be straight or branched chain and, like the cycloaliphatic compounds, saturated or unsaturated. The cycloaliphatic and the aromatic compounds include both mononuclear and polynuclear structures; the hydroxysulfonic acids according to the invention include aliphatic-aromatic and also aromatic-aliphatic compounds. Useful heterocyclic compounds encompass saturated and unsaturated five- and six-membered rings containing nitrogen, oxygen, or sulfur as the hetero atom. The molecule can contain one or two hetero atoms which may be the same or different. The heterocyclic radical can, moreover, be fused to another heterocyclic five- or six-membered ring or to a benzene ring. All the compounds can also carry further substituents which the expert knows to be inert in the reaction.

Y in the above formula is, in particular, a straight or branched chain saturated aliphatic radical having 2 to 20 carbon atoms, a mono- or dinuclear cycloaliphatic radical having 5 to 12 carbon atoms, or a mon- or dinuclear aromatic radical. The aromatic radicals are preferably derived from benzene, biphenyl, naphthalene, or binaphthyl. A particularly suitable alkylaryl is the readily available benzyl radical. Arylalkyl radicals are preferably based on toluene, ethylbenzene, or xylene. Of the heterocyclics, radicals of nitrogen-containing saturated or unsaturated five- or six-membered rings, in particular pyridine, are of importance.

The free hydroxysulfonic acids, which are available, for example, from their salts by ion exchange, can be employed to prepare the hydrolytically stable organic phosphites by the novel process. However, it is also possible to use water-soluble hydroxysulfonic acid salts of the formula $(MO_3S)_n-Y-(OH)_m$ as the starting substances; these are converted into the free hydroxysulfonic acid by reaction with an acid. In this formula, M is a hydrogen ion, an alkali metal ion, or an ammonium ion of the formula $[NR_4]^-$, wherein the R's are hydrogen and/or the same or different straight or branched chain alkyl radicals having 1 to 4 carbon atoms. M can be the equivalent of an alkaline earth metal ion, lead ion, or copper ion. The acid is usually employed in a stoichiometric amount, based on the sulfonate. However, slightly more or less than the stoichiometric amount of acid causes no problems. It has proved appropriate to use 0.8 to 1.2 equivalents of acid per equivalent of metal. All strong acids, in particular mineral acids, such as $H_2SO_4$, HCl, $HNO_3$, $H_3PO_4$, HF, and $HBF_4$, are suitable for the reaction, $H_2SO_4$ being preferred; the acids are normally employed as aqueous solutions.

To convert the hydroxysulfonates into the free hydroxysulfonic acids, water and aqueous acids are added to the hydroxysulfonate solution, while maintaining a temperature of 0° to 90° C., in particular 20° to 40° C., until the reaction mixture contains 0.5% to 80% by weight, preferably 25% to 35% by weight, of hydroxysulfonate, based on the solution. The concentration of the aqueous acid is 0.1 to 5 mol/liter, preferably 1 to 2 mol/liter.

The above described aqueous solution of the hydroxysulfonic acid can be further processed immediately, i.e. reacted with an amine. Water-insoluble amines which are used according to the invention are aliphatic, cycloaliphatic, aromatic, araliphatic, or heterocyclic compounds, preferably straight or branched chain aliphatic amines having a total of 10 to 60, in particular 12 to 36 carbon atoms. Hydroxysulfonate amines which have only a limited solubility, if any, in the organic solvent are less suitable. Examples of particularly suitable amines are: tri-n-octylamine, tri-isooctylamine, tri-2-ethylhexylamine, methyl-di-octylamine and tridodecylamine.

The amines are dissolved in water-insoluble organic solvents. Particularly suitable solvents are aliphatic or aromatic hydrocarbons or hydrocarbon mixtures, for example, toluene or kerosene-like fractions, as well as ethers having 8 to 20 carbon atoms.

The concentration of amine in the solution is 0.5% to 35% by weight, preferably 10% to 30% by weight and, in particular, 15% to 25% by weight, based on the solution. 0.5 to 1.5 mols, preferably 0.8 to 1.2 mols, of amine are used per equivalent of sulfonic acid. The use of excess amine ensures that only small losses of yield occur. Although an excess of amine higher than that described can be used, it does not lead to any improvement in separation, purification, or yield.

The reaction of the hydroxysulfonic acid with the amine is carried out by intensive mixing of the aqueous acid solution with the solution of the amine in the organic solvent at room temperature; it is not essential to use higher temperatures, but in some cases this provides advantages. When the reaction has ended, the phases are separated. The organic phase of lower specific gravity, which contains the amine salt, is dried. Suitable desiccants are $MgSO_4$ or $NaSO_4$, and residual traces of water can be removed by treatment in a water separator.

In the last step of the multi-stage synthesis, the ammonium salt of the hydroxysulfonic acid dissolved in an organic solvent, is reacted with an organic phosphite or a phosphorus-halogen compound. The transesterification (alcoholysis) of the phosphite is carried out at temperatures between 20° and 200° C., in particular 80° and 160° C., under normal atmospheric or reduced pressure. Although it is possible to use one of the two reactants in excess, the hydroxysulfonate and phosphite are usually reacted in equivalent amounts. The alcohol radicals in the phosphite can, in this way, also be replaced successfully by hydroxysulfonate to form mixed esters.

The reaction is accelerated by catalysts, for example amines, sodium alcoholates, aluminum trichloride, titanic acid esters, or phosphorous acid dialkyl esters. The amine used for salt formation with the hydroxysulfonic acid is preferably used as the catalyst also. It is therefore advisable to react the hydroxysulfonic acid with an excess of 1% to 10% over the stoichiometrically required amount of amine. In practice, the reactants hydroxysulfonate, organic phosphite, and catalyst are mixed and the alcohol or phenol liberated from the organic phosphite is distilled off from the reaction mixture. It has proved particularly appropriate to carry out the distillation in a falling film evaporator under greatly reduced pressure.

Compounds of the formula $(R^2O)_3P$ can be employed as the organic phosphites which are converted into esters of the hydroxysulfonates by alcoholysis. The $R^2$'s are the same or different and are optionally substituted aliphatic or aromatic hydrocarbon radicals, preferably having 1 to 12 carbon atoms. Examples of such phosphites are trimethyl phosphite, triethyl phosphite, n-butyl diethyl phosphite, tri-n-propyl phosphite, tri-n-butyl phosphite, tri-2-ethylhexyl phosphite, tri-n-octyl phosphite, tri-n-dodecyl phosphite, dimethyl phenyl phosphite, diethyl phenyl phosphite and triphenyl phosphite. The preferred compound is triphenyl phosphite.

As an alternative to the route described above, it is also possible for phosphorus-halogen compounds to be reacted with the ammonium salts of hydroxysulfonic acids to prepare phosphites which are stable to hydrolysis. Particularly suitable phosphorus-halogen compounds are the phosphorus trihalides ($PCl_3$, $PBr_3$ and $PI_3$), especially $PCl^3$, and ester-halides of phosphorus acids of the formula $(R^3O)PX_2$. In this formula, $R^3$ is an optionally substituted aliphatic, cycloaliphatic, or aromatic hydrocarbon radical, and X is chlorine, bromine, or iodine. The hydrocarbon radicals preferably contain 1 to 12 carbon atoms. Examples of useful hydrocarbon radicals $R^3$ are methyl, ethyl, n-propyl, n-butyl, i-butyl, 2-ethylhexyl, n-octyl, n-dodecyl, and phenyl. The phenyl radical is particularly suitable.

The reaction of the ammonium salt, dissolved in an organic solvent, of the hydroxysulfonic acid with the phosphorus-halogen compound is carried out at temperatures between 20° and 200° C., 80° to 160° C. being preferred. The reactants are usually allowed to react with one another under normal pressure, but either increased or reduced pressure can nevertheless be used. It is advantageous for the phosphorus-halogen compound to also be dissolved in a solvent, preferably that used for the hydroxysulfonic acid. The starting substances are in general allowed to react with one another in equivalent amounts, i.e. one OH group is reacted per halogen atom. In the case of phosphorous acid esterhalides, transesterification of the $R^3O$ radical is also possible. An excess of one of the two reactants causes no trouble, but may lead to a higher expenditure during purification of the ammonium salts of the hydroxysulfonic acid.

When the reaction has ended, the mixture is distilled for complete removal of the hydrogen halide formed in the course of the reaction and, if appropriate, the alcohol, the phenol, the organic solvent, and excess starting substances which may be present. The desired compound is usually obtained in high purity as the residue of the distillation.

Organic phosphites which are stable to hydrolysis and have the formula shown below are of particular importance. In some cases, they contain structural constituents of dyestuff molecules, and starting substances for their preparation will therefore be found amongst the intermediate products of dyestuff synthesis, for example naphtholsulfonic acids, such as Schaeffer's acid and Neville-Winter's acid, naphtholdisulfonic acids, such as G-acid and R-acid, and dinaphtholdisulfonic acids, such as chromotropic acid.

One group of important organic phosphites which is stable to hydrolysis corresponds to Formula 2

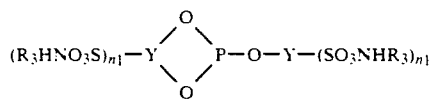

in which the Y's are independently the same as in Formula 1. The $n_1$'s are independently integers from 0 to 4, provided that at least one $n_1$ is at least 1. The R's are independently aliphatic, aromatic, araliphatic, homocyclic, or heterocyclic radicals. Preferably, the R's are straight or branched chain alkyl radicals, the sum of the three R's being 10 to 60, preferably 12 to 36, carbon atoms.

The compounds corresponding to the Formula 2 include ammonium sulfonates of trialkyl phosphites, such as trimethyl phosphite, triethyl phosphite, butyl diethyl phosphite, tri-n-propyl phosphite, tri-n-butyl phosphite, tri-2-ethylhexyl phosphite, tri-n-octyl phosphite, and tri-n-dodecyl phosphite, of dialkyl aryl phosphites, such as dimethyl phenyl phosphite and diethyl phenyl phosphite, of alkyl diaryl phosphites, such as methyl diphenyl phosphite and ethyl diphenyl phosphite, and of triaryl phosphites, such as triphenyl phosphite and trinaphthyl phosphite. The preferred phosphite of this group is triphenyl phosphite-trisulfonic acid triisooctylammonium salt.

Another group of important organic phosphites which are stable to hydrolysis are represented by Formula 3.

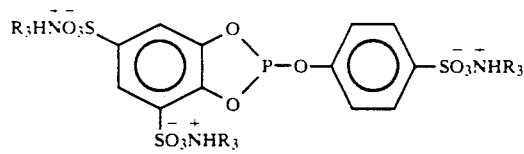

In this formula, the Y's are the same as in Formula 2, and are preferably radicals derived from benzene, biphenyl, naphthalene, or binaphthyl. The $n_1$'s and R's are as given under Formula 2.

Preferred ammonium sulfonates of phosphites according to Formula 3 are:

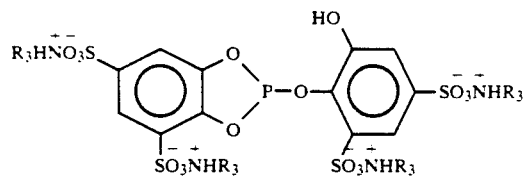

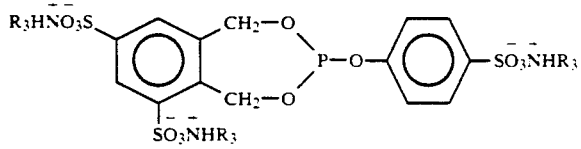

-continued
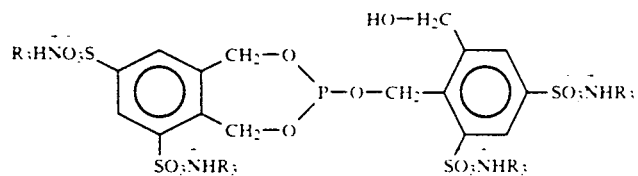
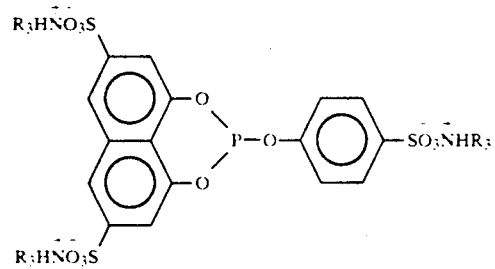
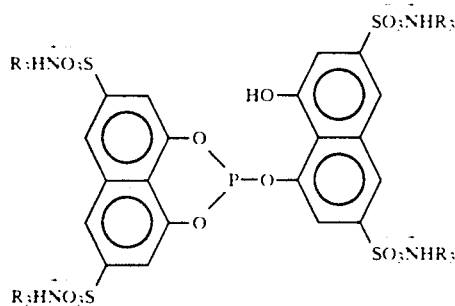
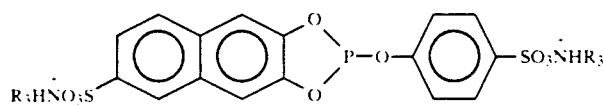
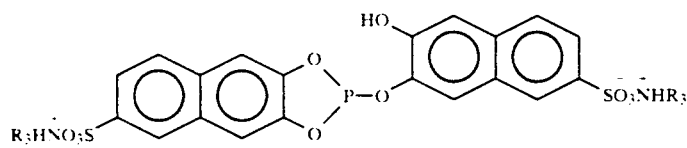
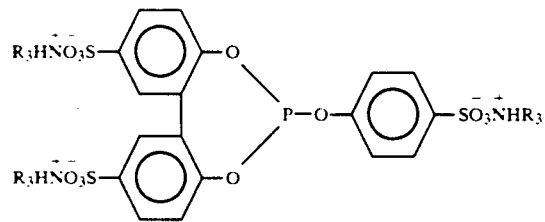
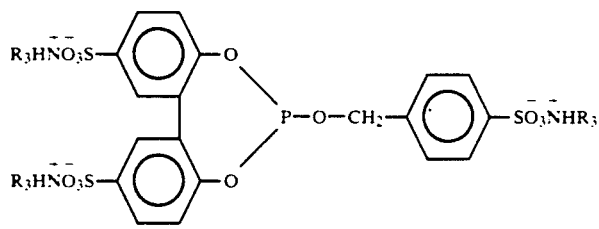

-continued

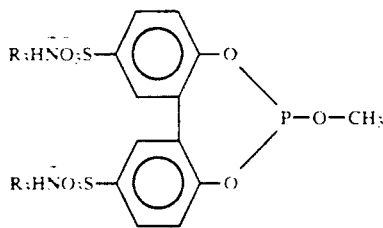

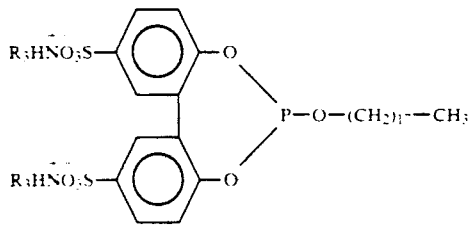

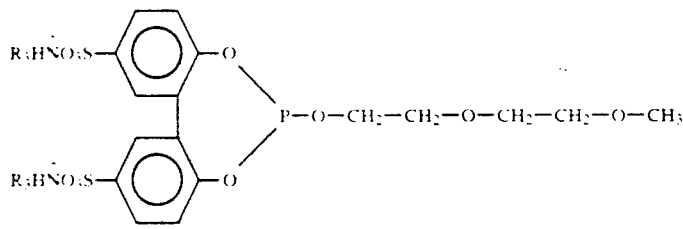

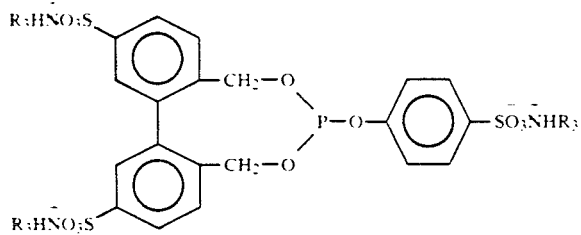

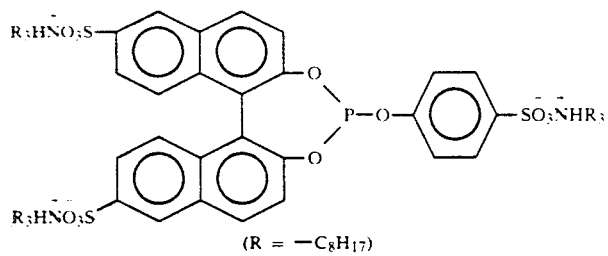

(R = —C$_8$H$_{17}$)

Additional important phosphites are those of Formula 4.

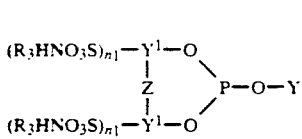

In this formula, Y has the meaning given in Formula 1 and the Y$^1$'s are independently arylalkyl, alkylaryl, aryl, biaryl, naphthyl, or binaphthyl radicals, in particular benzene. Z is —CH$_2$—, —(CH$_2$)$_2$—, or —(CH$_2$)$_3$—, and R and n$_1$ are as defined in Formula 2.

The preferred ammonium sulfonates of phosphites according to Formula 4 are:

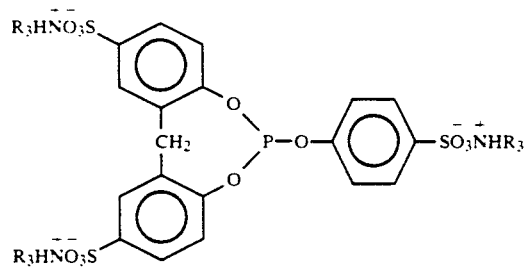

-continued

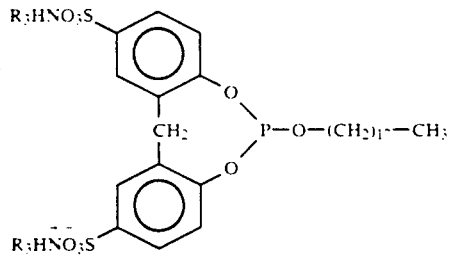

Finally, the phosphites of Formula 5 prepared by the process according to the invention are also of great interest.

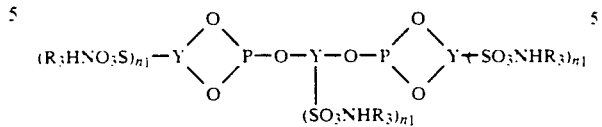

The Y's are as defined in Formula 2, in particular radicals derived from benzene, biphenyl, naphthalene, or alkanes having 2 to 6 carbon atoms. R and $n_1$ have the meanings given under Formula 3.

The preferred ammonium sulfonates of phosphites corresponding to the Formula 5 are:

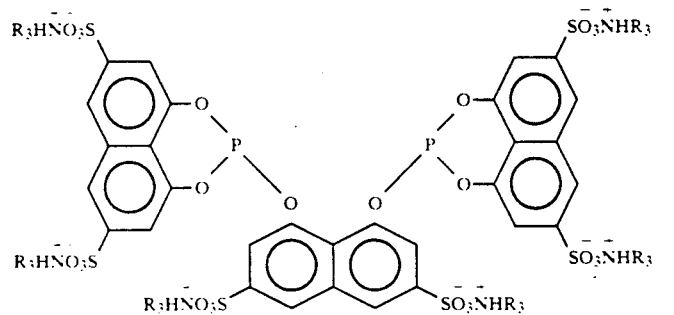

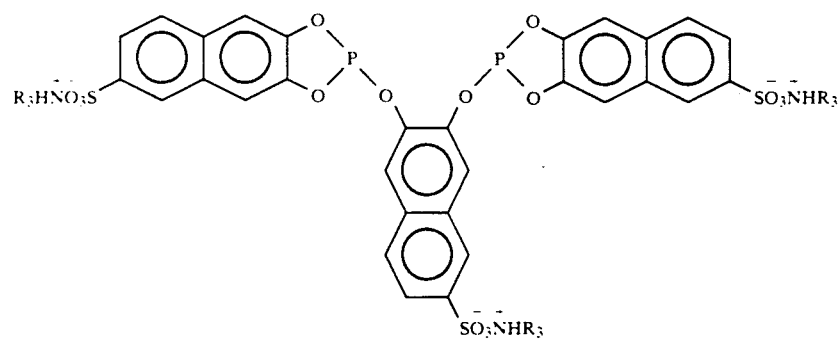

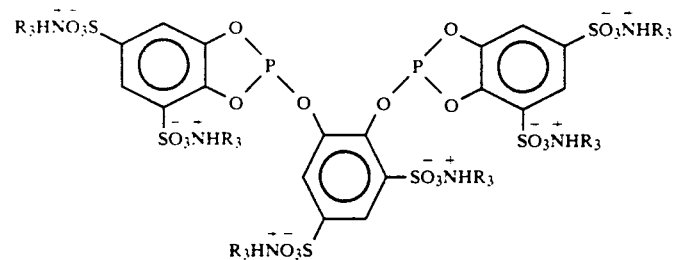

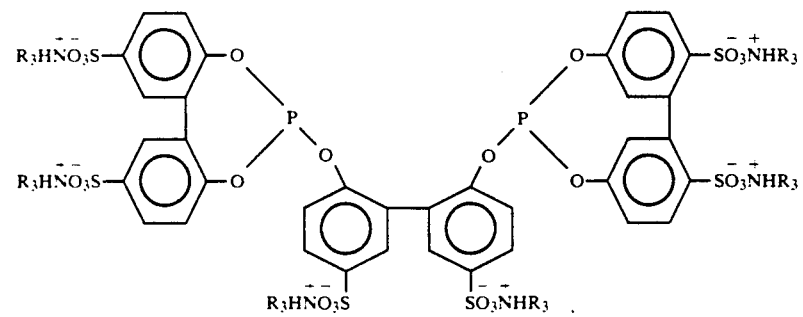

-continued

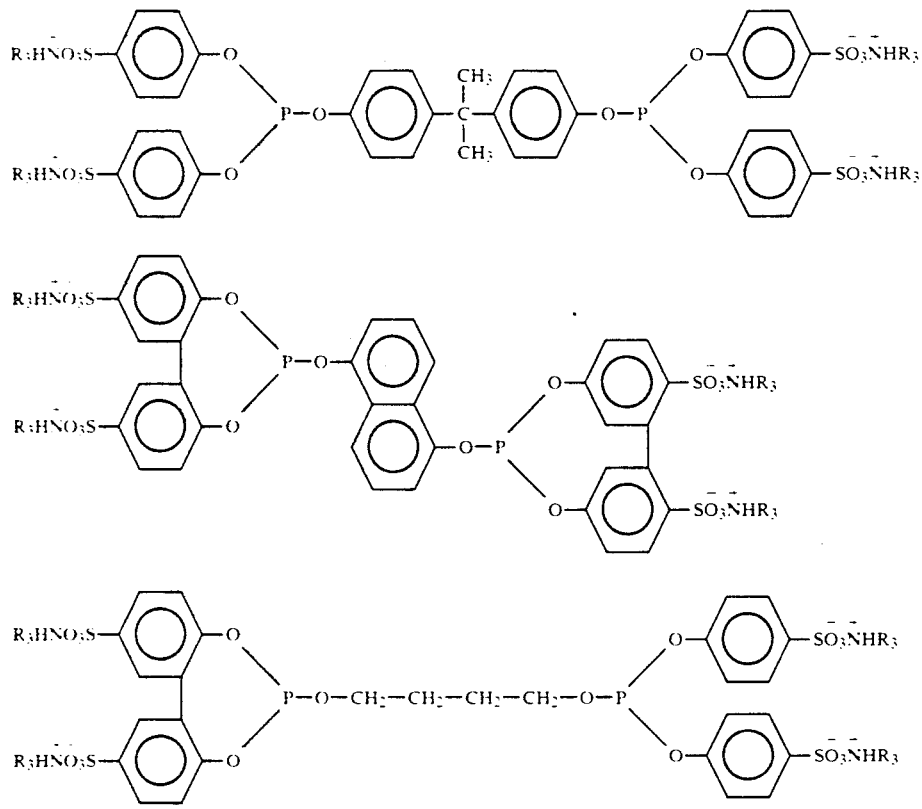

SPECIFIC EXAMPLES OF THE INVENTION

The following examples illustrate the invention, but do not limit it.

The following abbreviations are used:

| | |
|---|---|
| TPPpTS | triphenyl phosphite-trisulfonic acid |
| TPPpDS | triphenyl phosphite-disulfonic acid |
| TPPpMS | triphenyl phosphite-monosulfonic acid |
| TIOA | trisooctylamine |

EXAMPLE 1

Preparation of TPPpTS-TIOA, TPPpDS-TIOA and TPPpMS-TIOA 160.7 g of 65% aqueous 4-hydroxybenzenesulfonic acid solution (which corresponds to 104.5 g or 0.6 mol of acid) and 150 ml of distilled water are initially introduced into a 2 liter three-necked flask equipped with a stirrer, thermometer, dropping funnel, and reflux condenser; the flask has first been heated thoroughly and filled with argon. A solution of 211.8 g (0.6 mol) of TIOA in 500 ml of toluene is added dropwise to this solution and the mixture stirred for 3 hours. The lower colorless aqueous phase is separated off and discarded. The orange-colored TIOA/toluene layer is dried overnight with activated $Na_2SO_4$, the desiccant is then filtered out and the filtrate is heated for 12 hours, using a water separator; 8.5 g of water are removed.

A solution of 62.5 g (0.2 mol) of triphenyl phosphite and 5 g (0.01 mol) of TIOA in 150 ml of absolute toluene is added dropwise to the dried TIOA/toluene solution at an oil bath temperature of 140° C. over one hour, while cooling under reflux. The mixture is then distilled. Toluene first passes over at 110° C., followed by 29 g of phenol at 78° C./2.27 kPa (17 mm Hg) over 16 hours, and a further 14 g of phenol at 30° C./133.3 Pa (1 mm Hg) over 8 hours. Finally, unreacted triphenyl phosphite is distilled off at 65° C./1.3 Pa (0.01 mm Hg). A yellow viscous substance remains and is characterized by means of $^{31}$P-NMR, $^{1}$H-NMR, IR spectroscopy, and high pressure liquid chromatography (HPLC). Yield: 245.6 g = 76% of theory. The reaction product has the following composition on the basis of the $^{31}$P-NMR spectrum:

TPPpTS-TIOA:33%
TPPpDS-TIOA:46%
TPPpMS-TIOA:21%.

ANALYSES

A. $^{31}$P-NMR (200 MHz, $CDCl_3$ as the solvent, 85% by weight phosphoric acid as the external standard). δTPPpTS-TIOA = +127.5 ppm, δTPPpDS-TIOA = +128.0 ppm, δTPPpMS-TIOA = +128.4 ppm, δ(triphenyl phosphite) = +128.8 ppm (in traces).

B. $^{1}$H-NMR (80 MH$_2$, $CDCl_3$)

| δ/ppm | Split | Integral/cm | Proton |
|---|---|---|---|
| 7.85 | d | 0.55 | $H_a$ |
| 7.3–7.05 | m | 1.9 | $H_b$ |
| 3.01 | m | 2.1 | $H_c$ |
| 1.83–0.7 | m | 17.7 | $H_d$ |

-continued

| δ/ppm | Split | Integral cm | Proton |
|---|---|---|---|

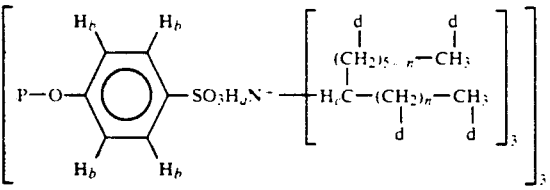

(n = 1-3)

C. IR spectrum (KBr pressed disk): 2960-2840 cm$^{-1}$ vCH, 1590-1485 cm$^{-1}$ vC=C, 1465 cm$^{-1}$ δ—CH$_3$, 1240-1160 cm$^{-1}$ and 1030 cm$^{-1}$ —SO$_3$, 1240-1160 cm$^{-1}$ P—O—Q.

D. HPLC analysis: (RP8 column, solvent ratio methanol/H$_2$O=90/10) RT=2.22 and 2.55 minutes, at RT=4.78 minutes traces of triphenyl phosphite are detectable (RT=retention time).

Hydrolysis of TPPpTS-TIOA, TPPpDS-TIOA and TPPpMS-TIOA

The course of the hydrolysis of TPPpTS-TIOA, TPPpDS-TIOA and TPPpMS-TIOA in acetone at 56° C. compared with the hydrolysis of triphenyl phosphite under the same conditions is analyzed by $^{31}$P-NMR spectroscopy.

A. Hydrolysis in the presence of a solvent (a) Triphenyl phosphite 1.675 g (93.06 mmol) of distilled water are added to a solution of 0.962 g (3.10 mmol) of triphenyl phosphite in 10 ml of acetone (dried over CaCl$_2$). This mixture is heated to 56° C. under reflux, with vigorous stirring. A sample is removed at intervals of one hour in each case and the progress of the hydrolysis is analyzed by means of $^{31}$P-NMR spectroscopy.

| Result Hours | 1 | 2 | 3 |
|---|---|---|---|
| Hydrolysis products in (%) | 19.8 | 97.0 | 100 |

(b) TPPpTS-TIOA, TPPpDS-TIOA, TPPpMS-TIOA 1.675 g (93.06 mmol) of distilled water are added to a solution of 5.0 g (3.10 mmol) of TPPpTS-TIOA (mixed with TPPpDS- and TPPpMS-TIOA) in 10 g of acetone (dried over CaCl$_2$) and the mixture is further treated as described under (a).

| Result Hours | 1 | 2 | 3 | 4 | 5 | 24 |
|---|---|---|---|---|---|---|
| Hydrolysis products in (%) | 2.5 | 6.5 | 7.4 | 15.7 | 19.1 | 100 |

B. Hydrolysis of triphenyl phosphite and of triphenyl phosphite-trisulfonic acid triisooctylammonium salt without a solvent at 25° C.

(a) Triphenyl phosphite 10 g (32.2 mmol) of triphenyl phosphite are stirred with 20 g (1.11 mol) of distilled water in a glass beaker at 25° C. for about half an hour. As the $^{31}$P-NMR spectrum shows, the triphenyl phosphite is hydrolyzed after 18 hours.

(b) TPPpTS-TIOA, TPPpDS-TIOA, TPPpMS-TIOA 10 g (6.2 mol) of TPPpTS-TIOA (mixed with TPPpDS- and TPPpMS-TIOA) are stirred with 20 g (1.11 mol) of distilled water in a glass beaker at 25° C. for about half an hour. As the $^{31}$P-NMR spectrum shows, TPPpTS-TIOA is hydrolyzed to the extent of only 6.3% within 18 hours.

EXAMPLE 2

Preparation of o-phenylene phosphite hexasulfonic acid-hexa(triisooctylammonium) salt 332.22 g (1.0 mol) of pyrocatechol-3,5-disulfonic acid disodium salt monohydrate (Tiron monohydrate) in 600 ml of distilled water are initially introduced into a 4 liter three-necked flask equipped with a stirrer, thermometer, and reflux condenser. 450 ml of 2M H$_2$SO$_4$ are added dropwise to this solution and the mixture is stirred intensively for 2 hours with cooling. A mixture of 707.36 grams (2 mol) of triisooctylamine in 900 ml of toluene is then added dropwise, with cooling, and the mixture is stirred overnight. The lower aqueous layer is separated off and discarded. The Tiron/triisooctylamine/toluene layer is then dried over Na$_2$SO$_4$, 200 ml of toluene are added, and the mixture is heated under reflux overnight using a water separator. 14 g of water are separated off. A solution of 206.8 g (0.666 mol) of triphenyl phosphite and 10 g (0.028 mol) of TIOA in 600 ml of absolute toluene is added dropwise to the mixture at an oil bath temperature of 150° C. in the course of 3 hours. When the addition has ended, the mixture is boiled under reflux for a further hour and is then distilled. Toluene initially passes over, followed by 124 g of phenol at 30° C./133.3 Pa (1 mm Hg) over 70 hours. Excess triphenyl phosphite cannot be distilled off. A yellow, very viscous substance remains, which is characterized by means of $^{31}$P-NMR spectroscopy. Yield: 672 g=66% of theoretical (based on the phenol distilled off).

Analysis:

$^{31}$P-NMR (200 MHz, CDCl$_3$, 85% by weight phosphoric acid external standard), δ (o-phenylene phosphite-hexasulfonic acid triisooctylammonium salt)= +130.6 ppm, δ (triphenyl phosphite)= +128.9 mmp (traces).

EXAMPLE 3

Preparation of o-phenylene phosphite-hexasulfonic acid triisooctylammonium salt 200 ml of 2M H$_2$SO$_4$ are added dropwise to 20 g (60.2 mmol) of pyrocatechol-3,5-disulfonic acid disodium salt hydrate (Tiron monohydrate) in a 1 liter three-necked flask equipped with a stirrer, thermometer, and reflux condenser over 2 hours, while cooling intensively. A solution of 42.52 g (120.4 mmol) of TIOA in 175 g of toluene is added dropwise to the solution formed and the mixture is stirred for 3 hours. The layer containing aqueous sulfuric acid (lower layer) is separated off and discarded. The Tiron/TIOA-toluene layer is then dried over MgSO$_4$, 200 ml of toluene are added and the mixture is heated overnight using a water separator. 1.1 g (0.06 mol) of H$_2$O are separated off. A solution of 5.51 g (40.13 mmol) of PCl$_3$ in 100 ml of toluene is added dropwise to the mixture in the course of 1 hour. The oil bath temperature is 140° C. Evolution of HCl is to be observed over 3 hours. The color of the solution changes from yellow to red-brown. The mixture is heated under reflux for a total of 4 hours. After cooling to room temperature, argon is passed through the solution for 1 hour, while stirring vigorously, in order to remove last residues of HCl. The toluene is then distilled off. A red-brown, very viscous oil remains.

Analysis:

$^{31}$P-MNR (200 MHz, CDCl$_3$, 85% by weight phosphoric acid as the external standard), δ (o-phenylene phosphite-hexasulfonic acid triisooctylammonium salt) = +130.7 ppm.

At δ = +72.7 ppm, δ = +13.1 ppm, δ = −10.5 ppm, signals which arise from impurities are also detectable.

What we claim is:

1. A process for the preparation of a hydrolytically stable phosphite comprising reaction of an organic phosphite or a phosphorous-halogen compound of the formula PX$_3$ or (R$^3$O)PX$_2$ with at least a chemically equivalent amount of an ammonium salt of a hydroxysulfonic acid, in an organic said salt being substantially insoluble in water and soluble in said organic solvent, wherein X is chlorine, bromine, or iodine and R$^3$ is a substituted or unsubstituted aliphatic, cycloaliphatic, or aromatic hydrocarbon radical.

2. The process of claim 1 wherein said ammonium salt is the reaction product of an aqueous solution of said acid, or an acidified aqueous solution of a water soluble salt of said acid, with a solution of a water insoluble amine in a water insoluble organic solvent.

3. The process of claim 2 wherein said acid or said water-soluble salt is of the formula

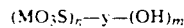

$(MO_3S)_n-Y-(OH)_m$ wherein Y is an organic radical, M is hydrogen, alkali metal ion, or ammonium ion of the formula [NR$_4$]$^-$, wherein R is independently hydrogen, straight or branched chain alkyl radicals having 1 to 4 carbon atoms, alkaline earth metal, lead, copper, or chemical equivalents thereof, m is an integer from 1–3, and n is an integer from 1–4.

4. The process of claim 2 wherein Y is a straight or branched chain saturated aliphatic radical having 2 to 20 carbon atoms; a mono- or dinuclear cycloaliphatic radical having 5 to 12 carbon atoms; a derivative of benzene, biphenyl, naphthalene, or binaphthyl; a benzyl radical, a radical derived from toluene, ethylbenzene, or xylene; or a radical derived from saturated or unsaturated nitrogen-containing five- or six-membered rings.

5. The process of claim 2 wherein H$_2$SO$_4$, HCl, HNO$_3$, H$_3$PO$_4$, HF, or HBF$_4$ are used to acidify said acidified acid solution.

6. The process of claim 2 wherein there are 0.8 to 1.2 mols of said amine per chemical equivalent of said acid.

7. The process of claim 1 wherein said ammonium salt is a derivative of a water-insoluble, straight or branched chain aliphatic amine having a total of 10 to 60 carbon atoms.

8. The process of claim 7 wherein said total is 12 to 36 carbon atoms.

9. The process of claim 2 wherein said organic solvent comprises toluene and/or kerosene-like hydrocarbon fractions.

10. The process of claim 1 wherein said reaction is carried out in the presence of a catalyst selected from the group consisting of sodium, an amine, sodium alcoholate, aluminum chloride, a titanic acid ester, and a phosphorous acid dialkyl ester.

11. The process of claim 1 wherein phenol is liberated during said reaction, said process further comprising continuous stripping off said phenol under vacuum in a thin film evaporator.

12. The process of claim 1 wherein said reaction is carried out at a temperature of 20° to 200° C.

13. The process of claim 12 wherein said temperature is 80° to 160°.

14. The process of claim 10 wherein said catalyst is an amine.

15. The process of claim 1 wherein there is a stoichiometric excess of said acid over said amine of 1 to 10%.

* * * * *